(12) United States Patent
Galea et al.

(10) Patent No.: US 8,876,743 B2
(45) Date of Patent: Nov. 4, 2014

(54) CONFORMABLE MATERIAL FOR AN ORTHOTIC DEVICE AND METHOD OF MAKING SAME

(75) Inventors: Anna M. Galea, Stow, MA (US); Kristen LeRoy, Somerville, MA (US); John Player, Wayland, MA (US)

(73) Assignee: Vivonics, Inc., Waltham, MA (US)

(*) Notice: Subject to any disclaimer, the term of this patent is extended or adjusted under 35 U.S.C. 154(b) by 209 days.

(21) Appl. No.: 13/506,428

(22) Filed: Apr. 18, 2012

(65) Prior Publication Data

US 2012/0271210 A1 Oct. 25, 2012

Related U.S. Application Data

(60) Provisional application No. 61/517,498, filed on Apr. 20, 2011.

(51) Int. Cl.
*A61F 5/00* (2006.01)

(52) U.S. Cl.
USPC ........................................ 602/5; 602/6; 602/7

(58) Field of Classification Search
CPC .... B32B 27/12; B32B 27/40; B32B 17/1077; B32B 2262/101; B32B 5/26; B32B 2260/023; B32B 5/024; B32B 17/02; B32B 1/00; B32B 5/04; B32B 23/00; B32B 2250/02; B32B 2262/106; B32B 2305/188; B32B 7/04; B32B 27/02; B32B 2305/18; B32B 2305/20; B32B 2305/28; B32B 2305/70; B32B 27/08; B32B 27/36; B32B 37/04; B32B 37/153; B32B 5/22; D04H 1/54; A61F 5/0123; A61F 2005/0139; A61F 2005/0174; A61F 2005/0181; A61F 2005/0137; A61F 2/80; A61F 2002/5083; A61F 2002/7818; A61F 2002/7862; A61F 2002/7881; A61F 2005/0158; A61F 2005/0167; A61F 2/7812; A61F 2002/5055; A61F 2/5046; A61F 2/78; A61F 2002/30065; A61F 2002/30069; A61F 2002/3021; A61F 2002/30324; A61F 2002/5007; A61F 2002/5053
USPC ............... 442/59, 344, 351; 602/41–54, 5–8; 128/889–890

See application file for complete search history.

(56) References Cited

U.S. PATENT DOCUMENTS

| | | | |
|---|---|---|---|
| 5,721,177 A * | 2/1998 | Frank | 442/59 |
| 6,733,845 B1 * | 5/2004 | Caramaro et al. | 427/477 |
| 7,195,729 B2 * | 3/2007 | Jackson et al. | 264/214 |
| 2003/0181989 A1 * | 9/2003 | Eberle et al. | 623/36 |
| 2007/0083136 A1 * | 4/2007 | Einarsson | 602/26 |

* cited by examiner

*Primary Examiner* — Michael A. Brown
(74) *Attorney, Agent, or Firm* — Iandiorio Teska & Coleman, LLP (57) ABSTRACT

A conformable material for an orthotic device including a plurality of fibers each including a plurality of filaments encapsulated by a first thermoplastic material. A second thermoplastic material is configured to bind the plurality of fibers and form the conformable material.

4 Claims, 8 Drawing Sheets

CONFORMABLE MATERIAL FOR AN ORTHOTIC DEVICE AND METHOD OF MAKING SAME

RELATED APPLICATIONS

This application claims benefit of and priority to U.S. Provisional Application Ser. No. 61/517,498 filed Apr. 20, 2011, under 35 U.S.C. §§119, 120, 363, 365, and 37 C.F.R. §1.55 and §1.78, incorporated herein by this reference.

GOVERNMENT RIGHTS

This invention was made with U.S. Government support under Contract No. W81XWH-09-C-0028 by the Army and Grant No. 1R43AR052985-01A2 from the National Institute of Health. The Government may have certain rights in certain aspects of the subject invention.

FIELD OF THE INVENTION

This invention relates to a conformable material for an orthotic device.

BACKGROUND OF THE INVENTION

The fit of the residual limb within a prosthetic socket is of primary concern for many amputees. A poor fit can lead to skin irritation, tissue breakdown, and discomfort. Poorly managed moisture at the interface between the residual limb and the prosthetic socket may result in infection, skin irritation and may decrease the usability of the prosthetic.

The volume of the residual limb of an amputee changes throughout the day, week, month, and year. Such volume fluctuations may lead to, inter alia, decreased comfort, increased shear forces, increased pressure on bony prominences, and a poor gait pattern. An uncomfortable or non-performing socket for a residual limb may also decrease user compliance.

Additionally, conventional splints for broken or sprained fingers, wrists, arms, ankles, feet, neck, back, and the like, do not always conform to the bony prominences of the aforementioned anatomical structures.

SUMMARY OF THE INVENTION

In one aspect, a conformable material for an orthotic device is featured including a plurality of fibers each including a plurality of filaments encapsulated by a first thermoplastic material. A second thermoplastic material is configured to bind the plurality of fibers and form the conformable material.

In one embodiment, the plurality of filaments may be made of a material configured to provide structure and tensile strength to the conformable material. The plurality of filaments may be made of glass or carbon. The first thermoplastic material may include a material configured to provide flexural modulus to the conformable material. The first thermoplastic material may include a low density polyethylene (LDPE). The second thermoplastic material may include a material configured to bind the plurality of fibers together. The second thermoplastic material may include a copolymer or Ethyl Vinyl Acetate. The melting point of the second thermoplastic material may be lower than the melting point of the first thermoplastic material. The conformable material may be shaped to form the orthotic device. The orthotic device may include a prosthetic socket liner. The combination of the plurality of fibers and the second thermoplastic material may be configured such that the prosthetic socket liner adapts to the changing conditions of a residual limb. The second thermoplastic material may be configured such that the prosthetic socket liner becomes more pliable as the temperature of a residual limb changes to provide a better fit of the prosthetic socket liner to the residual limb. The orthotic device may include a brace and/or a split. The combination of the plurality of fibers and second thermoplastic material may be configured such that the brace and/or splint may conform to bony prominences of the human body. The conformable material may be cut to form a plurality of strands. The plurality of strands may be woven and/or braided. The plurality of strands may be woven and/or braided an angle between about 0 degrees and about 90 degrees.

In another aspect, a method of manufacturing a conformable material for an orthotic device is featured, the method including the steps of heating and melting a first thermoplastic matrix material to form a plurality of sheets of the first thermoplastic, heating and melting a second thermoplastic material to form a plurality of sheets of the second thermoplastic material, sandwiching a sheet of filaments between the plurality of sheets of the first thermoplastic material, sandwiching the sheet of filaments and sheets of first thermoplastic material between the plurality of sheets of the second thermoplastic material, heating and melting the sandwiched sheets to form the conformable material for an orthotic device.

The method may include the step of cutting the conformable material into a plurality of stands. The method may include the step of braiding and/or weaving the plurality of stands together. The method may include the step of heating and melting the braided stands to form the conformable material having a predetermined shape.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
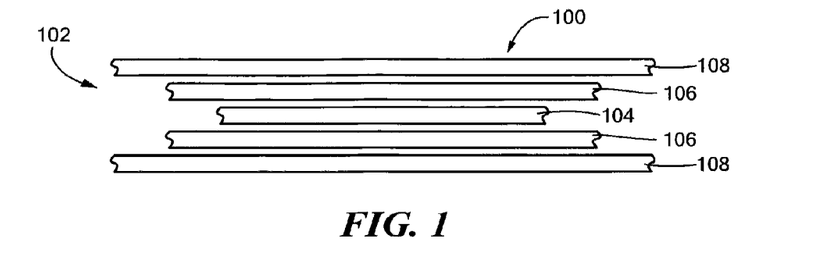
FIG. 1 is a schematic side-view showing the primary components of one embodiment of the conformable material for an orthotic device of this invention.

There is shown in FIG. 1 one embodiment of conformable material 100 for an orthotic device of this invention. Conformable material 100 includes a plurality of fibers each including a plurality of filaments encapsulated by a first thermoplastic material. A second thermoplastic material binds the plurality of fibers to form conformable material 100. For example, fiber 102 includes filament 104 encapsulated by first thermoplastic material 106. In one example, first thermoplastic material 106 may be a low density polyethylene (LPPE) material, or similar type material, which acts as the flexural modulus. In practice, each fiber 102 includes a plurality of filaments 104. Filaments 104 may be made of glass, carbon, or similar type material, which is preferably lightweight and provides structure and tensile strength. Filaments 104 may be extruded with a thermoplastic, e.g., a copolymer, to maintain the integrity of the otherwise fragile glass and to provide further structural rigidity.

Second thermoplastic material 108 binds fibers 102 made of filaments 104 and first thermoplastic material 106 together to form conformable material 100. Second thermoplastic material 108 may be ethylene vinyl acetate (EVA), or similar type material, which provides an appropriate amount of pliability while maintaining ductility. In one example, discussed in further detail below, conformable material 100 is cut into strands and processed to form conformable material 100, FIG. 2. In this example, second thermoplastic material 108 also acts to bind stands 110 of conformable material 100 at intersection of the stands, e.g., as indicated at 112. In this example, conformable material 100 is shown in with a unique braided design which provides distinctive stretching properties. In one design, strands 110 of conformable material 100 may be woven together in a biased formation at an angle between about 0 degrees and 90 degrees. In another design, strands 110 of conformable material 100 may be biased at an angle between about 40 degrees and about 50 degrees. In other examples, strands 110 of conformable material 100 may be biased at an angle between about 43 degrees and about 47 degrees. In one example, each of strands 110 of conformable material 100 have a width of about 3 mm and the distance between adjacent strands 110 of conformable material 100 is about 3 mm to about 5 mm. Conformable material 100 may be braided or woven, e.g., as shown in FIG. 2, or it may be wrapped, looped, or made in a similar type configuration.

Figure 2:
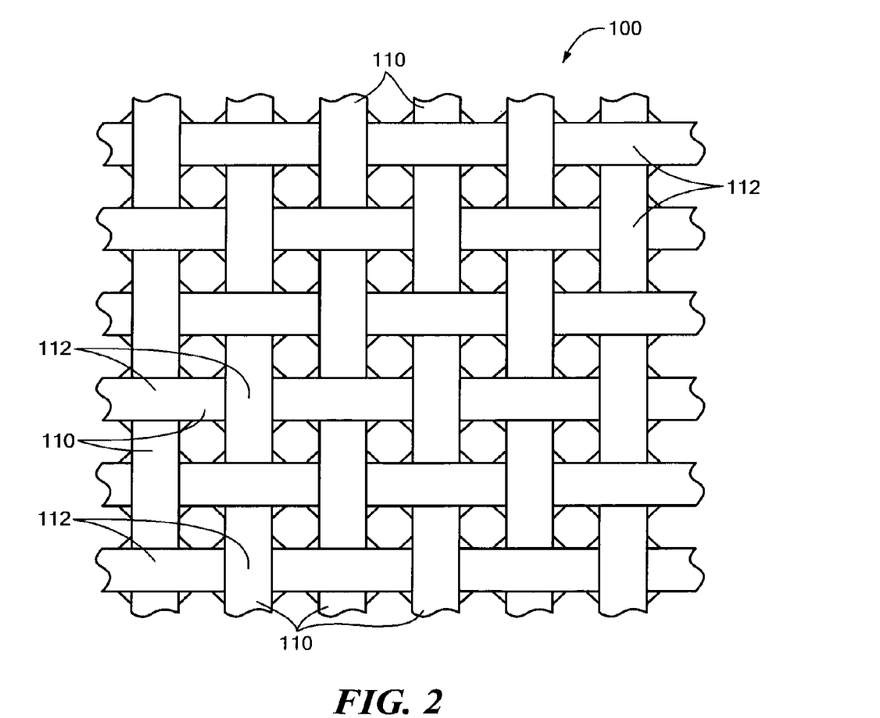
FIG. 2 is a three-dimensional top-view showing one embodiment of the conformable material for an orthotic device shown in FIG. 1.
Figure 3:
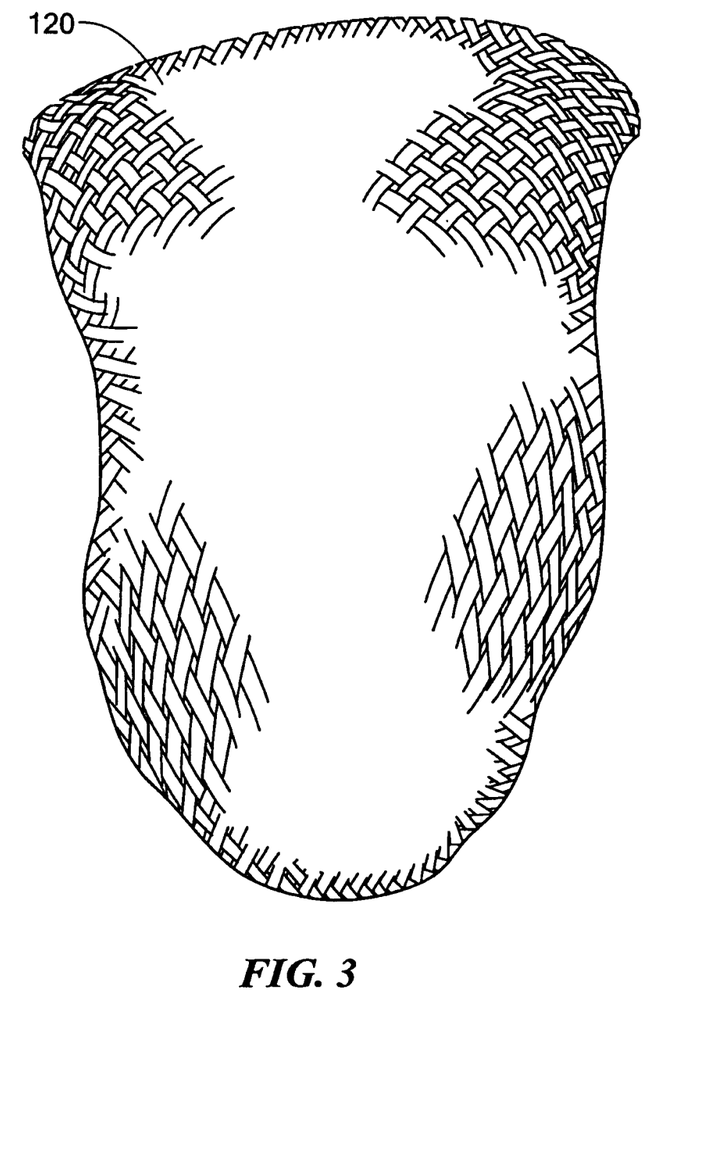
FIG. 3 is a three-dimensional front-view showing one embodiment of a prosthetic liner made of the conformable material shown in FIGS. 1 and 2.

In one example, conformable material 100, FIGS. 1 and 2, may be used to create an orthotic device, such as prosthetic liner 120, FIG. 3, for a prosthetic socket device. In this example, filaments 104, FIG. 1, are made of glass because it preferably reinforces first thermoplastic material 106 to form fibers 102. In this design, first thermoplastic material 106 and the reinforcing filaments 104 are assembled in a form known as pre-impregnated fibers. The individual reinforcing filaments 104 may be directly coated with first thermoplastic material 106 while in its molten fabrication temperature to form fibers 102. In this example, second thermoplastic material 108 binds fiber 102 together in a woven fashion to form a circular braid of conformable material 100 to create prosthetic liner 120, FIG. 3. As discussed above, second thermoplastic material 108 EVA. EVA is preferably soft enough such that to conform to the residual limb and the braided filaments 104 encapsulated by first thermoplastic 104 that forms fibers 102 provide structure and keep the flexural modulus prosthetic liner 120 strong enough to support the residual.

The result is prosthetic liner 120 adapts to changing conditions of a residual limb of an amputee. Prosthetic liner 120 conforms passively to the residual limb shape changes throughout day, week, month, and/or the year. Prosthetic liner 120 gently expands as body heat increase, accounts for any residual limb volume loss, and provides a snug fit. Prosthetic liner 120 is also preferably lightweight, breathable, and transparent to ultrasound.

Figure 4:
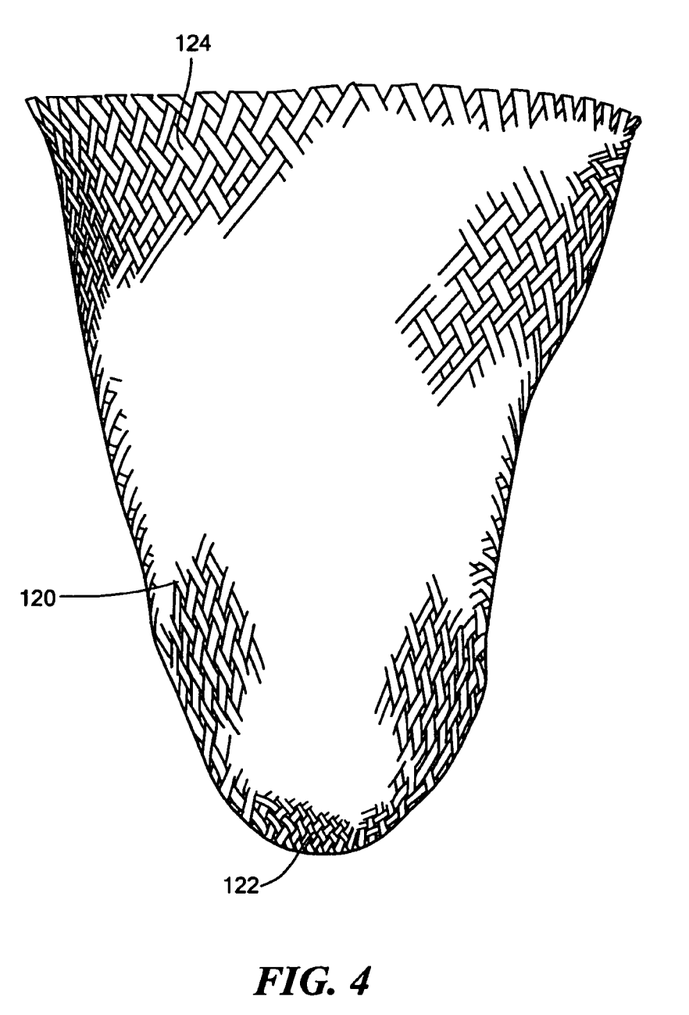
FIG. 4 is a three-dimensional side-view of the prosthetic liner shown in FIG. 3.
Figure 5:
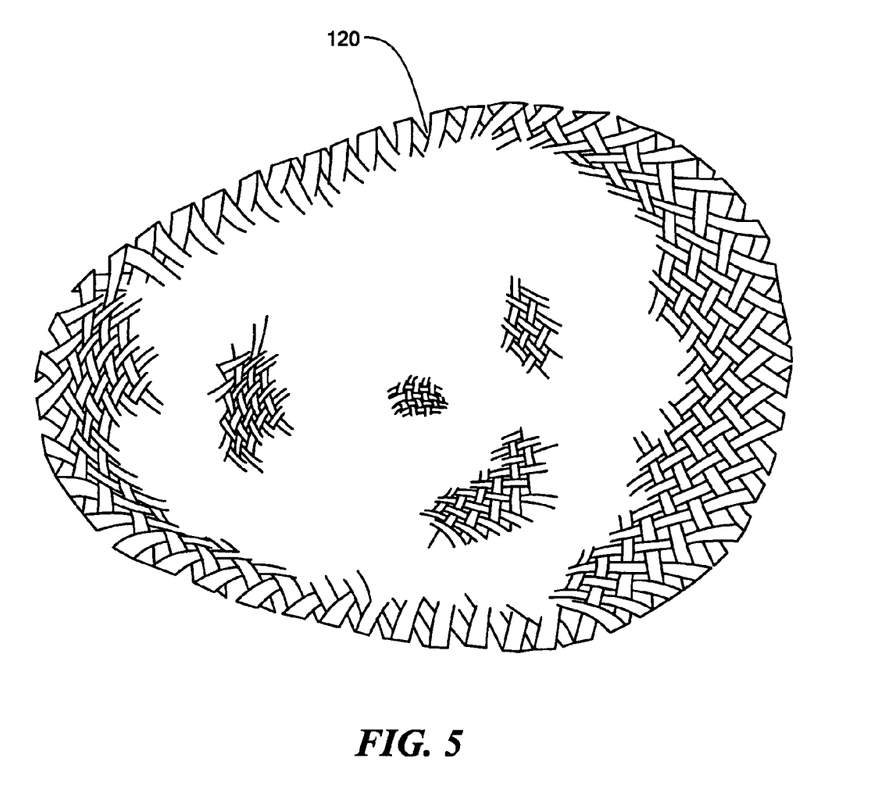
FIG. 5 is a three-dimensional top-view of the prosthetic liner shown in FIG. 3.
Figure 6:
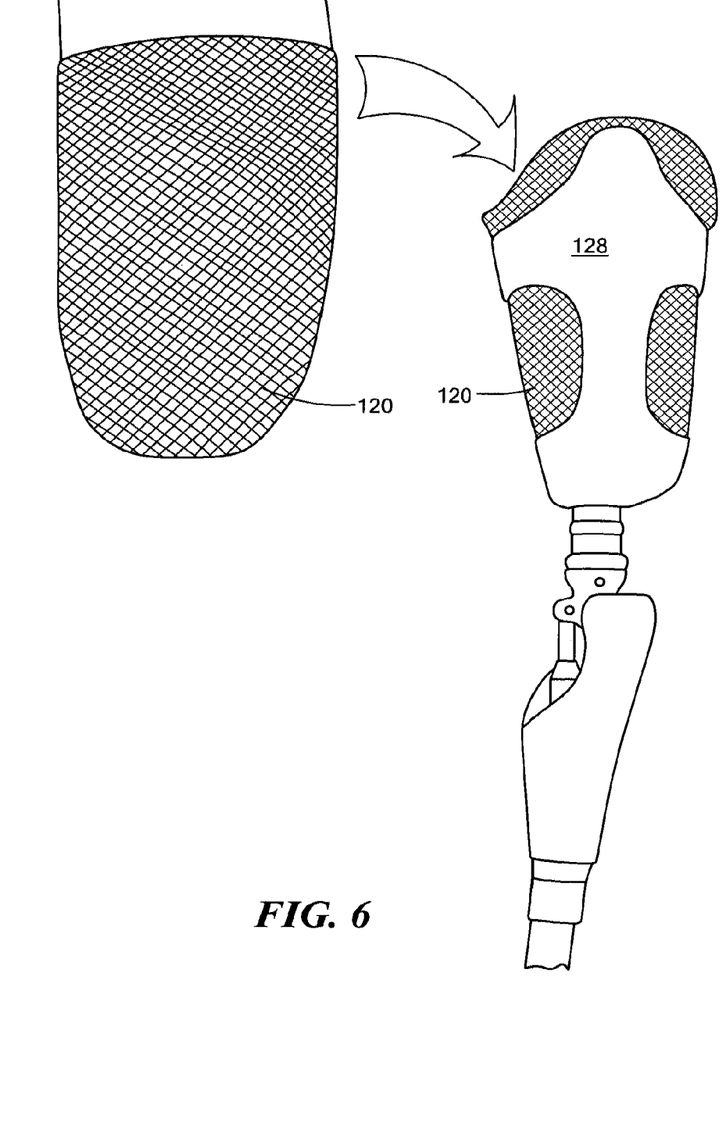
FIG. 6 shows three-dimensional views depicting one example of the conformable liner shown in FIGS. 3-5 in place in a prosthetic device.

FIG. 4 shows a side-view of liner 120 and FIG. 5 shows a top-view of liner 120. As shown in FIG. 4, second thermoplastic material 108 may be disposed more heavily at predetermined locations, e.g., bottom 122 of liner 120 and/or top 124 of liner 120 provide additional adaptively of prosthetic liner 120 for changing conditions of the residual limb. Ideally, prosthetic liner 120 changes its shape as it is worn. FIG. 6 shows one example of liner 120 in place in prosthetic device 128.

In other examples, conformable material 100, FIGS. 1 and 2, may be used to create an orthotic device, such as a splint and/or brace, which is adapted to conform to bony prominences of one or more of the wrist, hand, fingers, arms, legs, ankles, neck, back, and the like. For example, conformable material 100, FIG. 7, may be used to create splint 150 which adapts to bony prominences of the forearm, wrist and hand of a user as shown. In other examples, conformable material 100, FIG. 8, may be used to create a splint/brace 152 which conforms to the bony prominences of the forearm, wrist, and fingers as shown.

In this example, attachable material 111, e.g., gauze tape or hook and loops, may be used to assist keeping a tight fit around the user's leg or arm. In one design, conformable material 100 may be used to create splint 154, FIG. 8, for the fingers as shown, or splint 150, FIG. 9.

Figure 10:
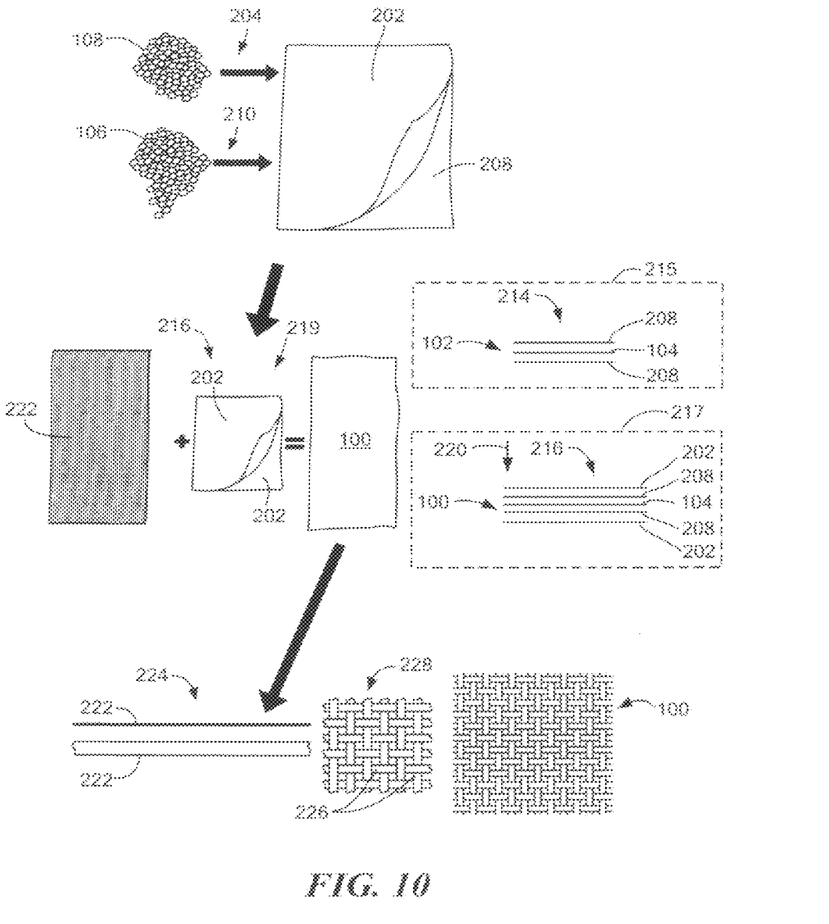
FIG. 10 shows a flowchart showing the primary steps of one embodiment of the method of manufacturing the conformable material in accordance with this invention.

One example of the method of manufacturing conformable material 100, FIGS. 1-9, is discussed below with reference to FIG. 10. In this example, second thermoplastic material 108, FIG. 1, e.g., EVA pellets 200, FIG. 10, is heated to form sheets 202 of second thermoplastic material 108, step 204. First thermoplastic material 106, e.g., LDPE pellets 206, is heated to form sheets 208 of first thermoplastic material 106, step 210. Sheet 212 of filaments 104 is then sandwiched between two sheets 208 of first thermoplastic material 106 to encapsulate filaments 104 therein and form fibers 102, step 214 (see cut-out 215). The sheet of filaments 104 encapsulated by first thermoplastic material 106 is the sandwiched between two sheets 202 of second thermoplastic material 108 to form conformable material 100, step 216 (see cut-out 217). Preferably, second thermoplastic material 108 has a melting point which is lower than the melting point of first thermoplastic material 106. Preferably, the layers of filaments 104 and first thermoplastic material 106 and sheets 202 of second thermoplastic material 108 are formed separately from each other due to the different melting points. Therefore, filaments 104 within first thermoplastic material 106 are heated and melted to form a new combination material. Then, filaments 104 and first thermoplastic material 106 are combined with sheets 202 of second thermoplastic material 108 through a separate heating/melting process. The layers are then pressed, indicated at 220 in cut-out 217, to form conformable material 100.

Conformable material 100 is then cut into strands, e.g., strand 222, step 224. A plurality of stands 226 is then braided or woven to form plaited sheet 226, step 228. Strands 226 are then placed into an oven at a high temperature to form conformable material 100. In one example, the temperature of the oven may be about 208 F to about 212 F. The oven may be under vacuum conditions.

Figure 7:
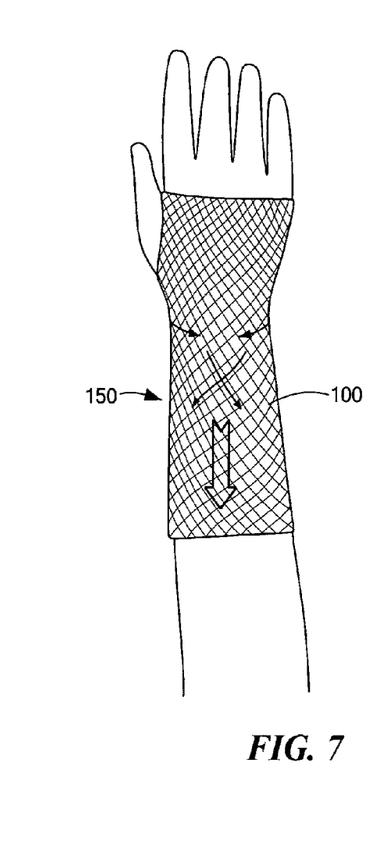
FIG. 7 is a schematic view showing one example of the conformable material shown in FIGS. 1 and 2 configured as a brace and/or splint.
Figure 8:
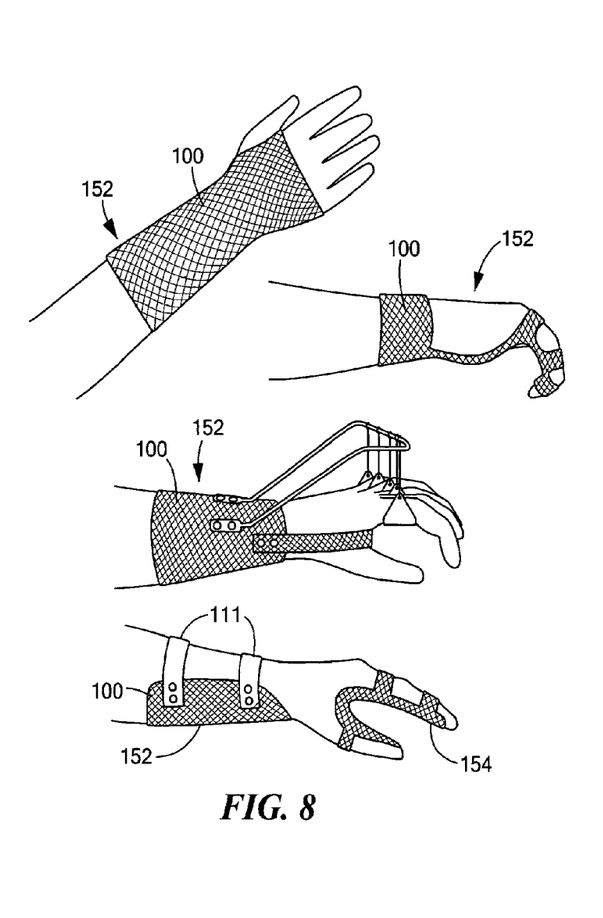
FIG. 8 depicts views of various embodiments of the conformable material shown in FIGS. 1 and 2 configured as a brace and/or splint for the wrist and fingers.
Figure 9:
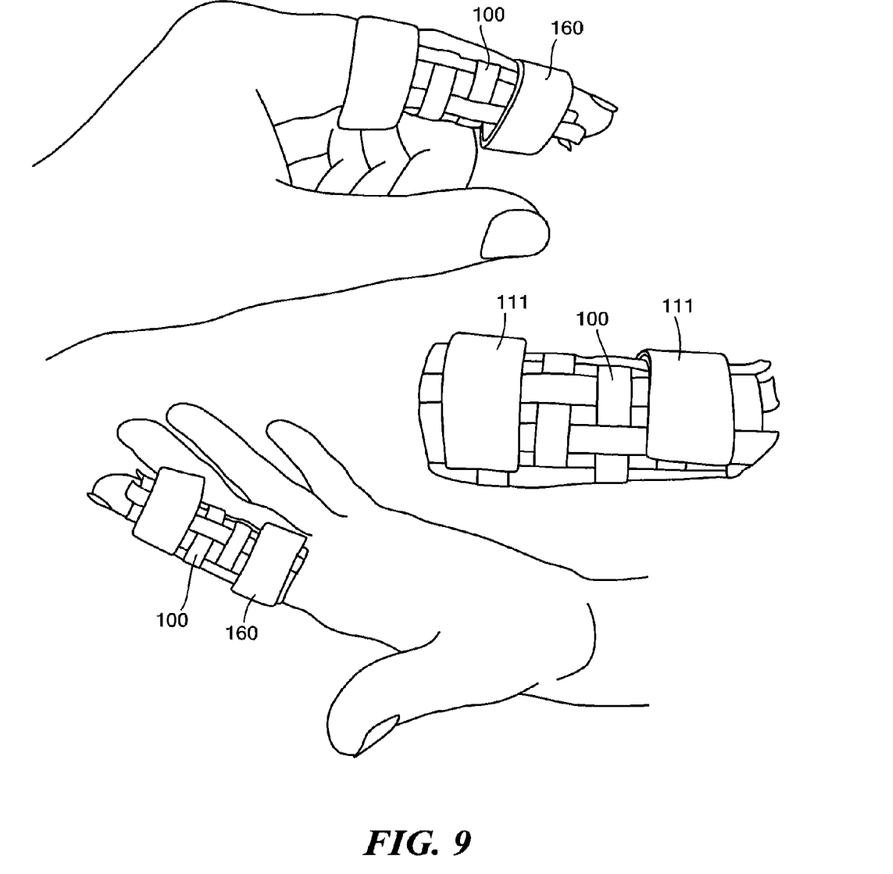
FIG. 9 shows three-dimensional views depicting one example of the conformable material shown in FIGS. 1 and 2 configured as a splint for a finger.

Step 228 of braiding or weaving the strands of conformable material may be performed by standard methods such as hand weaving or by automated braiding machines. Strands of conformable material 100 may be braided together into flat sheets or three-dimensional shapes. The flat braided sheets are preferably used for braces or splints, e.g., as shown in FIGS. 7-9. Three-dimensional shaped conformable material 100 may be used for prosthetic socket 106, FIGS. 3-6.

In one example, the conformable material 100 may be fabricated with 4 mm spacing and processed at 210° F. under vacuum conditions to create minimal fiber spreading, low EVA flow (interstitial spaces remained open) and adequate integration of the LDPE into the e-glass fibers.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A method of manufacturing a conformable material for an orthotic device, the method comprising the steps of:

heating and melting a first thermoplastic matrix material to form a plurality of sheets of the first thermoplastic;

heating and melting a second thermoplastic material to form a plurality of sheets of the second thermoplastic material;

sandwiching a sheet of filaments between the plurality of sheets of the first thermoplastic material;

sandwiching the sheet of filaments and sheets of first thermoplastic material between the plurality of sheets of the second thermoplastic material; and heating and melting the sandwiched sheets to form the conformable material for an orthotic device.

2. The method of claim 1 further including the step of cutting the conformable material into a plurality of stands.

3. The method of claim 2 further including the step of braiding and/or weaving the plurality of stands together.

4. The method of claim 3 further including the step of heating and melting the braided stands to form the conformable material having a predetermined shape.

* * * * *